(12) United States Patent
Morgan

(10) Patent No.: US 9,874,503 B2
(45) Date of Patent: Jan. 23, 2018

(54) SYSTEMS AND METHODS OF USE FOR DIGITALLY TESTING AND REPORTING THE PULL-OUT STRENGTH OF A FASTENER MEMBER

(71) Applicant: HYDRAJAWS, LIMITED, Birmingham, West Midlands (GB)

(72) Inventor: Adrian Morgan, Birmingham (GB)

(73) Assignee: Hydrajaws, Limited, Coleshill, Birmingham (GB)

( * ) Notice: Subject to any disclaimer, the term of this patent is extended or adjusted under 35 U.S.C. 154(b) by 0 days.

(21) Appl. No.: 15/177,479

(22) Filed: Jun. 9, 2016

(65) Prior Publication Data

US 2017/0315034 A1     Nov. 2, 2017

Related U.S. Application Data

(60) Provisional application No. 62/330,396, filed on May 2, 2016.

(51) Int. Cl.
    *G01L 5/24*            (2006.01)
    *G01N 3/08*           (2006.01)
    (Continued)

(52) U.S. Cl.
    CPC .............. *G01N 3/08* (2013.01); *G01N 3/066* (2013.01); *H04W 4/008* (2013.01); *H04W 84/12* (2013.01)

(58) Field of Classification Search
    CPC ..... G01L 5/00; G01L 3/00; G01L 3/06; G01L 3/08; G01N 3/34; G01N 33/383;
    (Continued)

(56) References Cited

U.S. PATENT DOCUMENTS 4,662,227 A * 5/1987 Peterson ............... G01L 5/0033
                                                         73/826
4,753,115 A      6/1988 Moody
               (Continued)

FOREIGN PATENT DOCUMENTS

EP        2 781 764 A1     9/2014
GB        2195453    *    4/1988
           (Continued)

*Primary Examiner* — Harshad R Patel
*Assistant Examiner* — Octavia Hollington
(74) *Attorney, Agent, or Firm* — James A. Sheridan; Sheridan Law, LLC

(57) ABSTRACT

Systems and methods of use pertaining to a digital testing and communication system for testing the pull-out strength of a fastener member secured within a base material. The system includes a mechanical screw/actuation arrangement configured to act through a load cell to apply an increasing tensile force to the fastener. The system also includes a digital load gauge in communication with the load cell and configured to indicate the tensile force measured by the load cell. The testing and communication system may incorporate a data system, a reporting system, and a transmission system configured compile the force information into a testing report along with location information, date and time information, and/or a pass-fail indication that is transmitted to/provided upon one or more client devices located on-site or at a remote location.

7 Claims, 10 Drawing Sheets

(51) Int. Cl.
*G01N 3/06* (2006.01)
*H04W 84/12* (2009.01)
*H04W 4/00* (2009.01)

(58) Field of Classification Search
CPC .......... G01N 33/03; G01N 33/10; G01N 3/08; G01N 3/066
USPC .................................. 73/761, 834, 826, 760
See application file for complete search history.

(56) References Cited

U.S. PATENT DOCUMENTS

| | | |
|---|---|---|
| 5,703,302 A | 12/1997 | Hasler et al. |
| 5,792,961 A | 8/1998 | Giebner et al. |
| 6,041,660 A | 3/2000 | Fujitaka et al. |
| 7,260,998 B2 | 8/2007 | Madden et al. |
| 8,752,428 B2 | 6/2014 | Akins et al. |
| 2006/0207337 A1 | 9/2006 | Madden et al. |
| 2015/0323402 A1 | 11/2015 | Clark |
| 2015/0328757 A1 | 11/2015 | Schwertner et al. |
| 2017/0102300 A1* | 4/2017 | Saleem ................. G01M 99/00 |
| 2017/0102304 A1* | 4/2017 | Saleem ................. G01N 33/383 |

FOREIGN PATENT DOCUMENTS

| | | |
|---|---|---|
| GB | 2 368 644 A | 8/2002 |
| WO | 2012/069691 A1 | 5/2012 |
| WO | 2014/090798 A1 | 6/2014 |
| WO | 2014/146738 A1 | 9/2014 |
| WO | 2015/136681 A1 | 9/2015 |
| WO | 2015/137519 A1 | 9/2015 |

* cited by examiner

Time elapsed scale

Load Over Time

SYSTEMS AND METHODS OF USE FOR DIGITALLY TESTING AND REPORTING THE PULL-OUT STRENGTH OF A FASTENER MEMBER

REFERENCE TO PENDING PRIOR PATENT APPLICATION

This application claims the benefit under 35 U.S.C. 119(e) of U.S. Provisional Patent Application No. 62/330,396, filed May 2, 2016 by Adrian Morgan for "DIGITAL PULL-OUT TESTER KIT," which patent application is hereby incorporated herein by reference.

BACKGROUND

Many factors affect the strength and durability of eyebolts, anchor bolts, lifelines, scaffold ties, stud anchors, resin bolts and safety wires, etc., making it vital that such fixings, fasteners, and anchors are regularly checked against required stress load levels. Oftentimes, a visual inspection is not sufficient, and pull-out testers are employed to gauge fixing/fastener integrity.

Pull-out testers enable engineers to confirm the holding power of fixings, fasteners, and anchors secured in most base construction materials. Pull-out testing is performed to establish the tensile strength of fasteners that have been installed or fitted into walls, ceilings, and/or other surfaces and are vital for commercial buildings, railways, airports, and more. Pull-out testing generally involves attaching a hand-held piece of equipment to a bolt, nut, screw, fixing, or other fastener member before pulling to the designated stress load level to determine how strong and secure the fixing is. This type of testing enables early diagnosis of potential strength problems before they become larger risks or liabilities.

FIG. 1 illustrates a perspective view of two technicians performing a fastener strength test according to the current standard of manual and analog pull-out testing, recording, and reporting, as it exists in the prior art. Currently, pull-out testing results are recorded via a manual process that requires the testing technician to take visual readings from an analog load gauge 10 and a corresponding stop watch 12 before manually recording those readings with pen and paper 14. Using this prior art method, proof or confirmation of testing is not available (e.g., date, time, duration or time frame, location, etc.), testing generally requires at least two technicians, and testing results and reporting are subject to human error, as well as delays required to electronically transcribe the results for client viewing.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a digital testing and communication system for testing a pull-out strength of a fastener member secured in a base material. The system may include (1) a load cell; (2) a mechanical actuation arrangement configured to engage with the fastener member and act through the load cell to apply a tensile force to the fastener member, the load cell configured to measure force information reflecting the tensile force applied to the fastener member; (3) a digital load gauge communicatively coupled with the load cell; (4) a data system, the data system including: (a) a global positioning system (GPS) receiver configured to track geolocation information associated with the testing; (b) a timing device configured to track date information and time information associated with the testing; and (c) a load and displacement module configured to analyze the force information measured by the load cell throughout the testing; (5) a transmission system, the transmission system configured to transmit the force information to a client device; and (6) a reporting system, the reporting system including a report-generation module configured to generate a testing report based on at least the force information.

Another embodiment provides a pull-out test system for the in situ tensile testing of a fastener member secured in a base material. The system may include (1) a load cell; (2) a mechanical screw arrangement configured to engage with the fastener member and act through the load cell to apply a tensile force to the fastener member, the load cell configured to measure the tensile force applied to the fastener member; (3) a data system communicatively coupled with the load cell, the data system configured to record a date of the testing, a time frame of the testing, a geolocation of the test system during the time frame of the testing, and the tensile force applied to the fastener member throughout the time frame of the testing; (4) a transmission system configured to transmit the force information to one or more client devices; and (5) a reporting system configured to generate a testing report based upon the tensile force applied to the fastener member throughout the time frame of the testing.

Yet another embodiment provides a method for strength testing a fastener member secured in a base material. The method may include (1) providing a portable pull-out test system comprising: (a) a load cell; (b) a mechanical screw arrangement configured to engage with the fastener member and act through the load cell to apply an increasing tensile force to the fastener member, the load cell configured to measure the tensile force applied to the fastener member; (c) a driving member configured to actuate the mechanical screw arrangement; (d) a digital load gauge communicatively coupled with the load cell; (e) a data system; (f) a transmission system; and (g) a reporting system. The method may continue with (2) engaging the mechanical screw arrangement with the fastener member; (3) actuating the driving member to generate the tensile force on the fastener member; (4) via the data system, recording a date of the testing, a time frame of the testing, a geolocation of the test system during the time frame of the testing, and the tensile force applied to the fastener member over the time frame of the testing; (5) via the data system, analyzing the tensile force measured by the load cell throughout the time frame of the testing; (6) via the transmission system, transmitting the tensile force to one or more client devices; and (7) via the reporting system, generating a testing report summarizing the testing.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
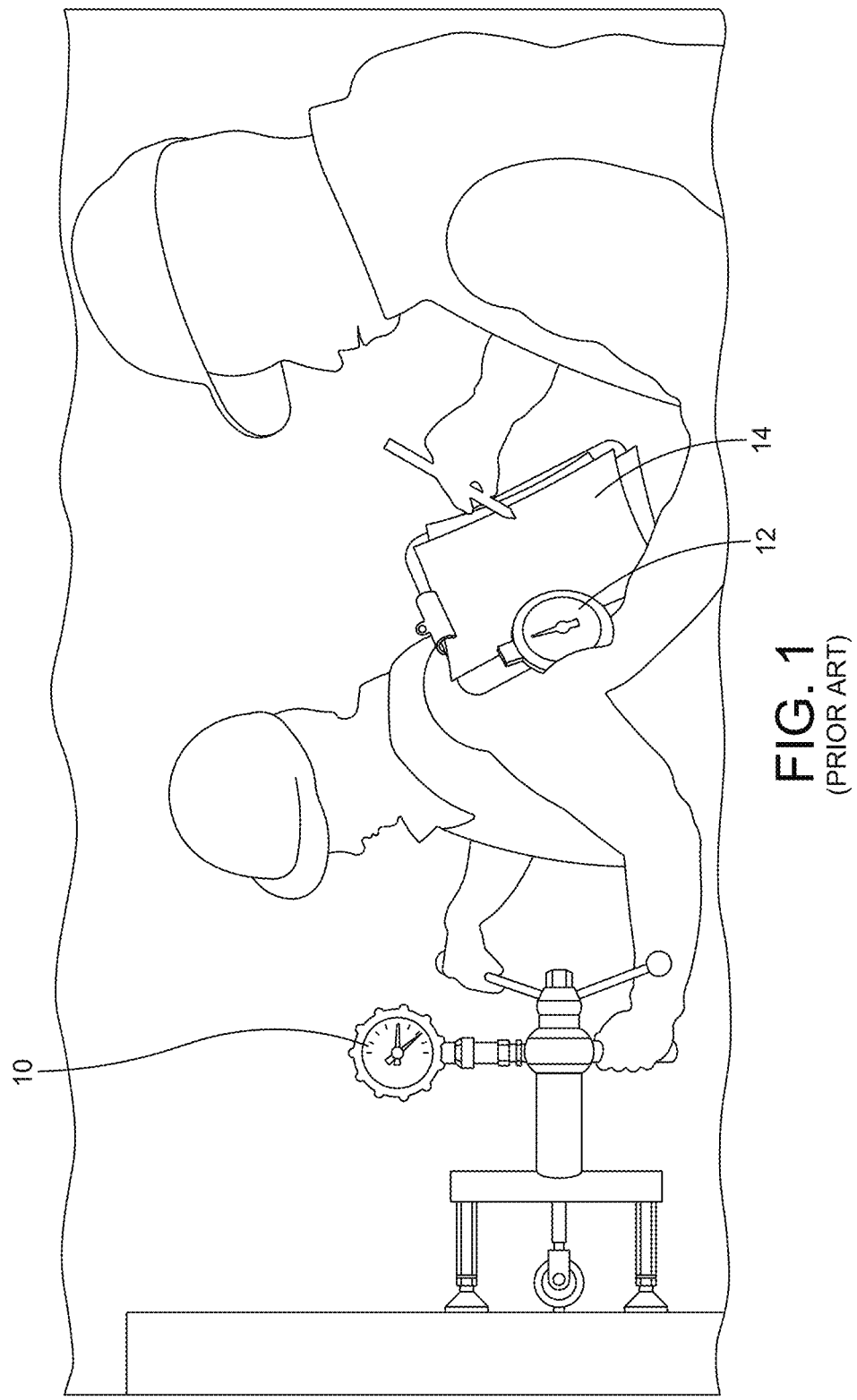
FIG. 1 illustrates a perspective view of two technicians performing a fastener strength test according to the current, prior art standard of manual and analog pull-out testing.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

When elements are referred to as being "connected" or "coupled," the elements can be directly connected or coupled together or one or more intervening elements may also be present. In contrast, when elements are referred to as being "directly connected" or "directly coupled," there are no intervening elements present.

The subject matter may be embodied as devices, systems, methods, and/or computer program products. Accordingly, some or all of the subject matter may be embodied in hardware and/or in software or in a combination thereof (including firmware, resident software, micro-code, state machines, gate arrays, etc.). As used herein, a software component may include any type of computer instruction or computer executable code located within or on a non-transitory computer-readable storage medium. A software component may, for instance, comprise one or more physical or logical blocks of computer instructions, which may be organized as a routine, program, object, component, data structure, etc., that performs one or more tasks or implements particular data types.

Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable storage medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. By way of example, computer readable media may comprise computer storage media and communication media.

Computer storage media/memory includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by an instruction execution system. Note that the computer-usable or computer-readable medium could be paper or another suitable medium upon which the program is printed, as the program can be electronically captured, via, for instance, optical scanning of the paper or other medium, then compiled, interpreted, of otherwise processed in a suitable manner, if necessary, and then stored in a computer memory.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

When the subject matter is embodied in the general context of computer-executable instructions, the embodiment may comprise program modules, executed by one or more systems, computers, or other devices. Generally, program modules include routines, programs, objects, components, data structures, etc. that perform particular tasks/functions or implement particular abstract data types. Typically, the functionality of the program modules may be combined or distributed as desired in various embodiments. Software implementations may include one or more computer programs comprising executable code/instructions that, when executed by a processor, may cause the processor to perform a method defined at least in part by the executable instructions. The computer program can be written in any form of programming language, including complied or interpreted languages, and can be deployed in any form, including as a standalone program or as a module, component, subroutine, or other unit suitable for use in a computing environment.

As may be appreciated, based on the disclosure, there exists a need for a portable pull-out testing system having the ability to record and communicate testing information, including, for example, testing date and time information, geolocation information, force information, displacement information, and an indication regarding whether the test passed or failed, to client devices located either locally at the testing site or remotely (e.g., at the client's office). Various embodiments of the systems and methods described herein relate to pull-out testing for fixings, eyebolts, ringbolts, lifelines, anchors, and other fasteners (hereinafter and collectively "fasteners" or "fastener members") secured, installed within, or affixed to a base material. More specifically, the disclosure details a digital pull-out tester and communication system that compiles test results on-site and provides a report that details the testing results, whether the test passed or failed, the date and time frame of the testing, and the testing location. The report may be immediately transmitted in real time to one or more on-site client devices via a Bluetooth transceiver/network or to one or more remote client devices via a Wi-Fi transceiver/network and/or a mobile cellular transceiver/network. The testing system allows for instant visual graphics, provided either on-site or remotely, and allows test technicians, engineers, clients, and other stakeholders to immediately confirm testing and analyze results.

Figure 2:
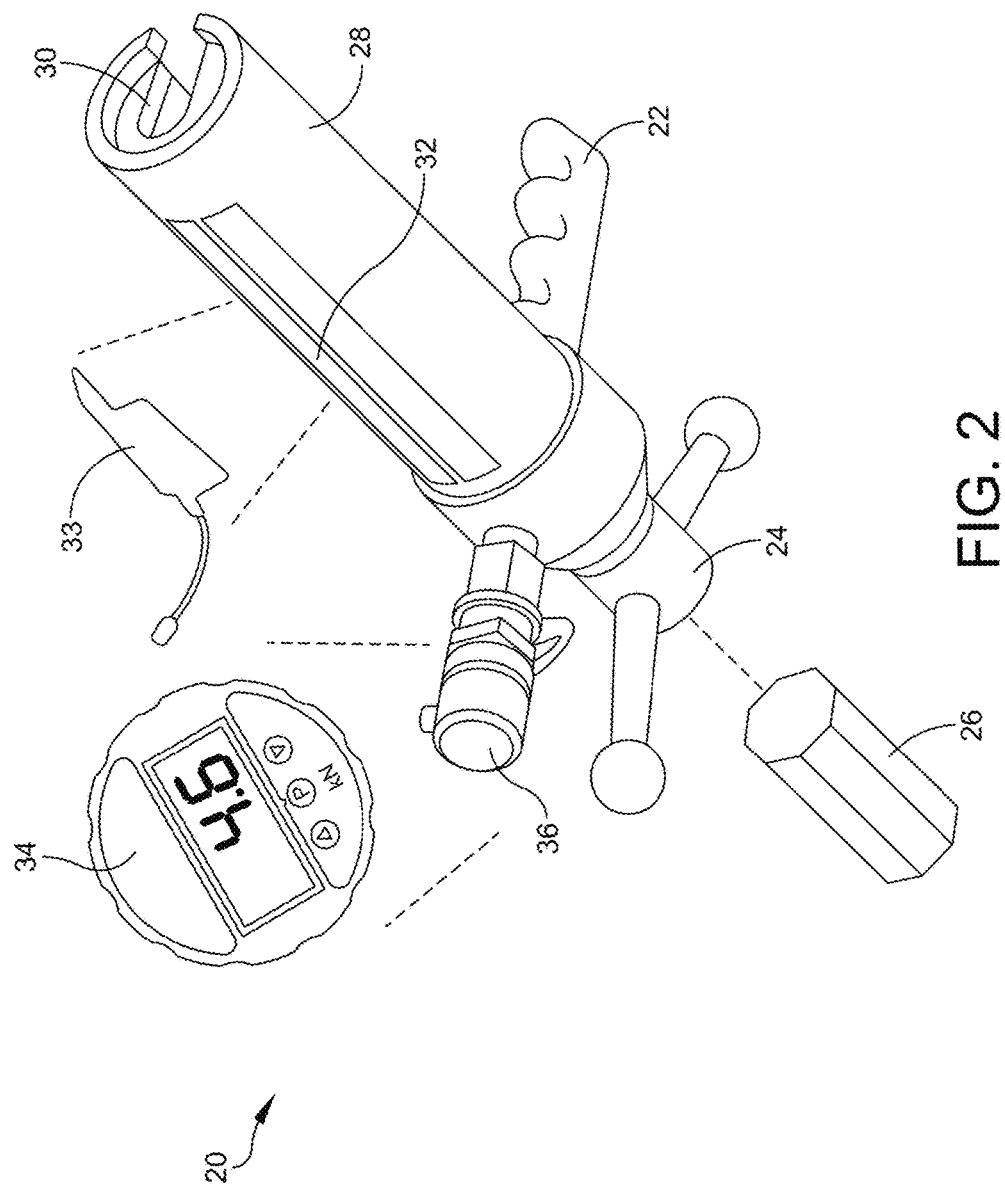
FIG. 2 illustrates an exploded view of one embodiment of a pull-out tester for testing the strength of a fastener secured in a base material.

FIG. 2 provides an exploded view of one embodiment of a pull-out tester 20. In this embodiment, the pull-out tester may include a handle grip 22 and a driving member or operating handle 24. The operating handle 24 may link to a mechanical screw arrangement, such as a hexagon operating nut 26 that integrates with operating handle 24, which is configured to act through a load cell 28 to apply a tensile force to the secured fastener being tested. Load cell 28 may feature a load jaw 30 and a movement or displacement indicator scale 32 to register a "first movement" on the fastener prior to the application of the test load (e.g., 50 mm or 100 mm displacement).

Pull-out tester 20 may also include a displacement sensor 33 in wired or wireless communication with a digital load gauge 34. In one embodiment, digital load gauge 34 may attach to pull-out tester 20 via a coupling 36 or via any other appropriate attachment mechanism that communicatively couples load cell 28 and digital load gauge 34, which may be configured to both visually indicate the applied tensile force, as measured by load cell 28, as well as transmit the applied tensile force to one or more on-site or remote client devices, as discussed below. Embodiments of digital load gauge 34 may also be configured to compile testing data and communicate testing reports to both on-site and remote client devices, as discussed below in relation to FIG. 4.

Tester 20 may be provided as part of a larger tester kit, which may include a variety of tester and/or fastener accessories (not shown). The accessories may be attached, for example, to the load jaw 30 or to the mechanical screw/actuation arrangement 26 of pull-out tester 20 and/or the fastener under test to increase the scope of possible testing applications. For example, the fastener may be fitted with a threaded or slotted button adapter that fits over the fastener and reconfigures the fastener for secure engagement with tester 20. Various adapters may be configured appropriately for the size and/or type of fastener under test (e.g., M4, M5, M6, M8, M10, and M12 threaded button adaptors; 4.5, 5.5, 6.5, 8.5, 10.5 & 12.5 mm slotted button adapters, threaded rod adapters, threaded stud adapters, insulation adapters, a ringbolt adapter clevis, etc.). Similarly, in one embodiment, load jaw 30 of tester 20 may be fitted with a tester adapter that corresponds with the type of fastener to be tested (e.g., a bolt tester adapter).

Figure 3:
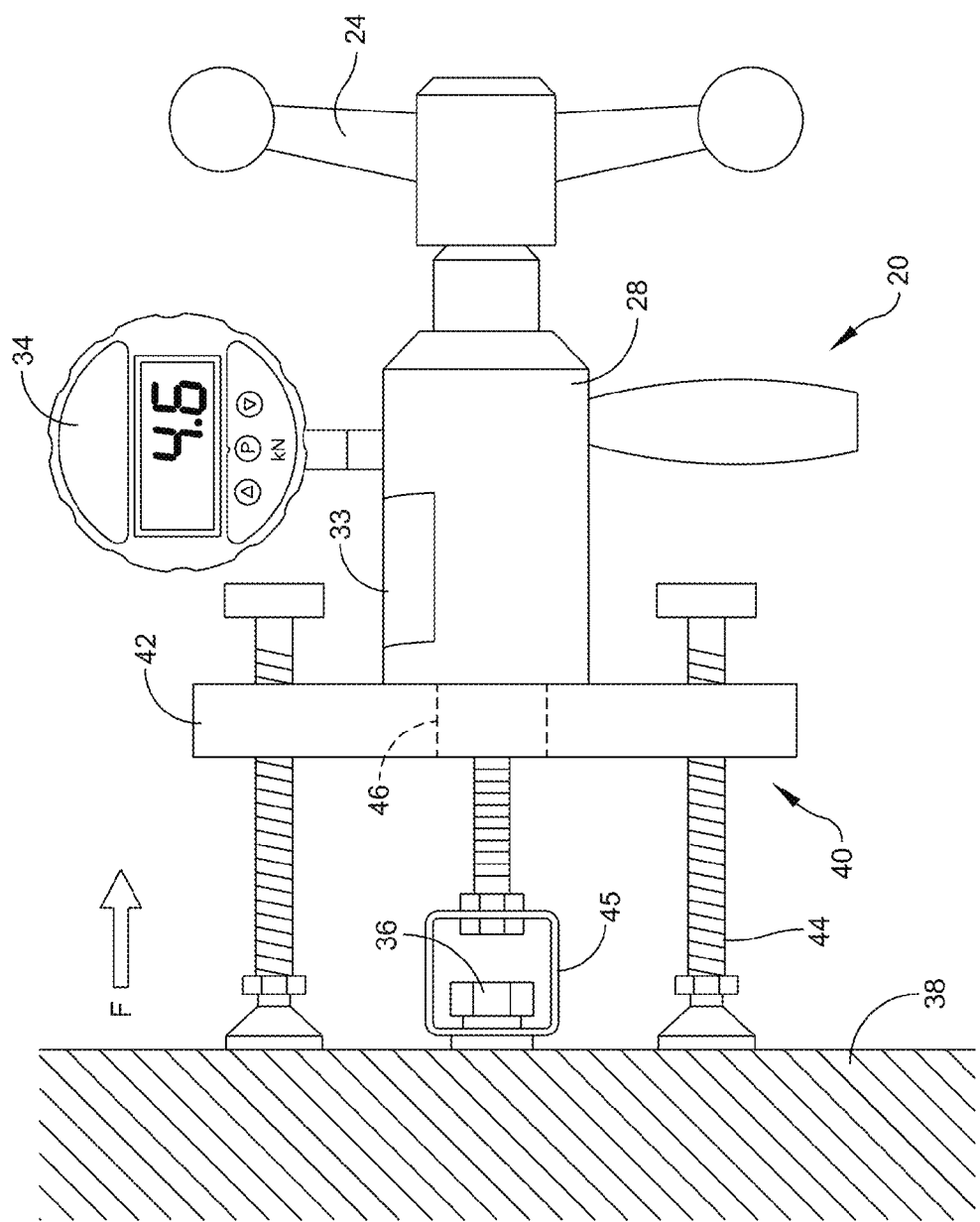
FIG. 3 illustrates a side view of the pull-out tester of FIG. 2 engaged with a fastener to be strength tested.

FIG. 3 illustrates a side view of one embodiment of tester 20 in operation, i.e., engaged with a fastener 36 that is secured within a base material 38. In this embodiment, the tester kit may include a load spreading bridge 40, which provides a leverage base for tester 20 and allows testing of the unsupported base material 38 surrounding fastener 36. Embodiments of load spreading bridge 40 may include a bridge portion 42 spanning a number of adjustable or telescopic legs 44, which may be adjusted until any tester adapter 45 of pull-out tester 20 can be passed through an opening 46 in bridge 42, such that the tester/tester adapter and the fastener/fastener adapter may align and engage. Legs 44 of load-spreading bridge 40 may be further adjusted until all legs 44 contact the base material, and the load spreading bridge is both aligned and level (according to bubble levels positioned on each face). In one embodiment, and once tester 20 and load spreading bridge 40 are in place, an increasing tensile load, F, may be applied to fastener 36 by turning operating handle 24 clockwise.

In one embodiment, load spreading bridge 40 may include three legs 44 and be configured to withstand tensile loads exceeding 3600 lbf without experiencing deformation, thereby enabling the testing of fall-protection anchors.

Digital load gauge 34 of tester 20, either independently or in a distributed manner in conjunction with a testing software application that may be downloaded and/or installed upon one or more client devices, may operate to collect, analyze, and wirelessly report a variety of testing data to the client devices. In one embodiment, tester 20, including digital load gauge 34 operating in communication with displacement sensor 33 and a testing application 51 running on one or more client devices, may comprise a digital testing and communication system 49, detailed in the block diagram of FIG. 4.

Generally, digital testing and communication system 49 may feature several components, including a load/displacement module, a location module, a timing device/clock, and logic instructions regarding the collection, analysis, and presentation or reporting of testing data to determine the success of the test and to present test confirmation information and test analytics in a user-friendly format for technicians, engineers, and clients. In this regard, system 49 may formulate a testing report that indicates the date, time, and location of the test, whether the test passed or failed based on predetermined test criteria, and present graphical information summarizing the load and/or displacement data.

Figure 4:
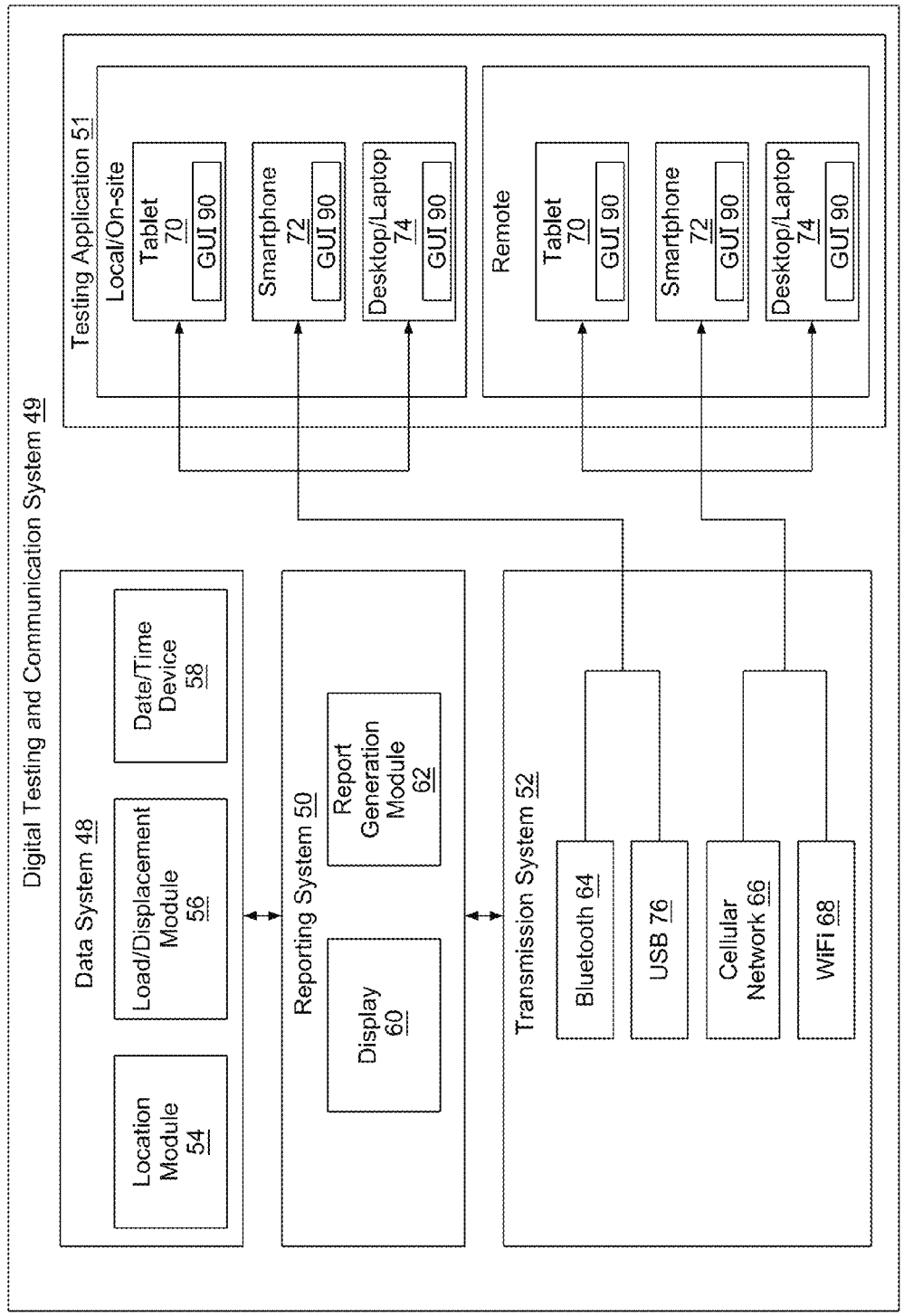
FIG. 4 provides a block diagram summarizing the functionality of numerous distributed components of one embodiment of a digital testing and communication system incorporating the pull-out tester of FIG. 2.

More specifically, FIG. 4 provides a block diagram summarizing a number of data collection, analysis, and reporting modules/subsystems of digital testing and communication system 49. Notably, the various components of system 49 described below may be distributed as appropriate (in whole or in part) across tester 20—including load cell 28, digital load gauge 34, and/or displacement sensor 33—as well as testing software application 51 running on one or more client devices 70, 72, 74. In one embodiment, system 49 may include a data system 48, a reporting system 50, and a transmission system 52. Each of data, reporting, and transmission systems 48, 50, 52 may include a number of components and/or functional modules that are distributed as appropriate about testing and communication system 49. In this embodiment, data system 48 may include a location module 54, a load and displacement module 56, and a timing device 58.

In further detail, timing device 58 may track date and time information associated with the testing, including, for example, a date of the testing and a time frame of the testing (e.g., a start time, a stop time, and a number of desired/varying time increments therebetween). Location module 54 may incorporate a GPS receiver and track geolocation information associated with tester 20, including a geolocation of tester 20 throughout the time frame of the testing. Load/displacement module 56 may record and/or analyze the force and/or displacement information measured by load cell 28 and displacement sensor 33, including comparing the increasing tensile load, F, applied to fastener 36 to a set of predetermined test criteria required of fastener 36.

Figure 5A:
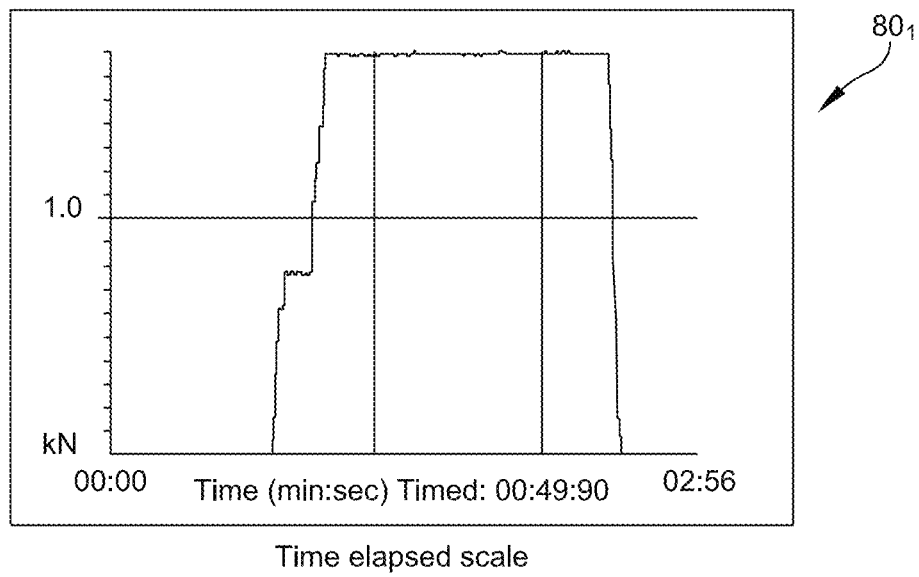
FIGS. 5A-5C provide screenshots showing exemplary testing reports generated via the digital testing and communication system of FIG. 4.
Figure 5B:
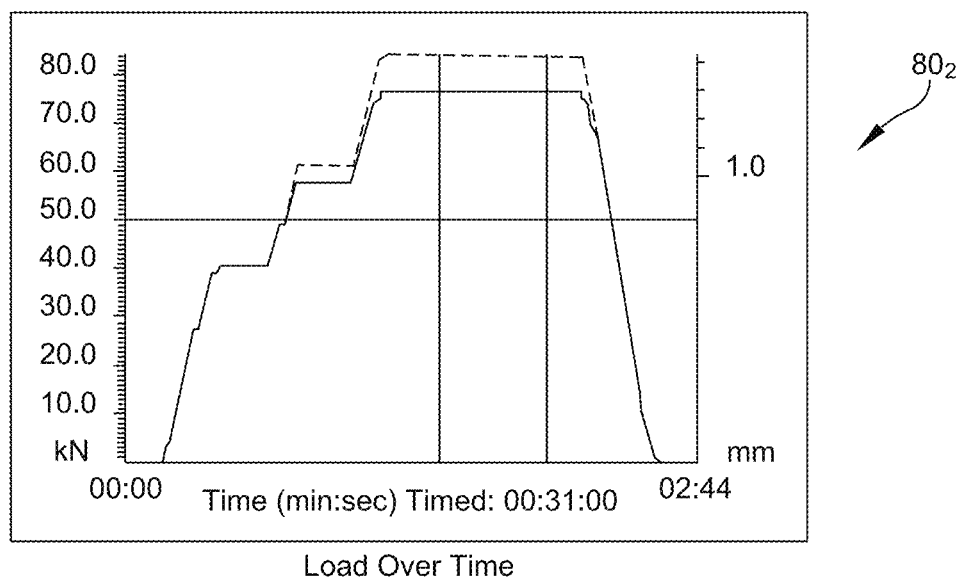
Figure 5C:
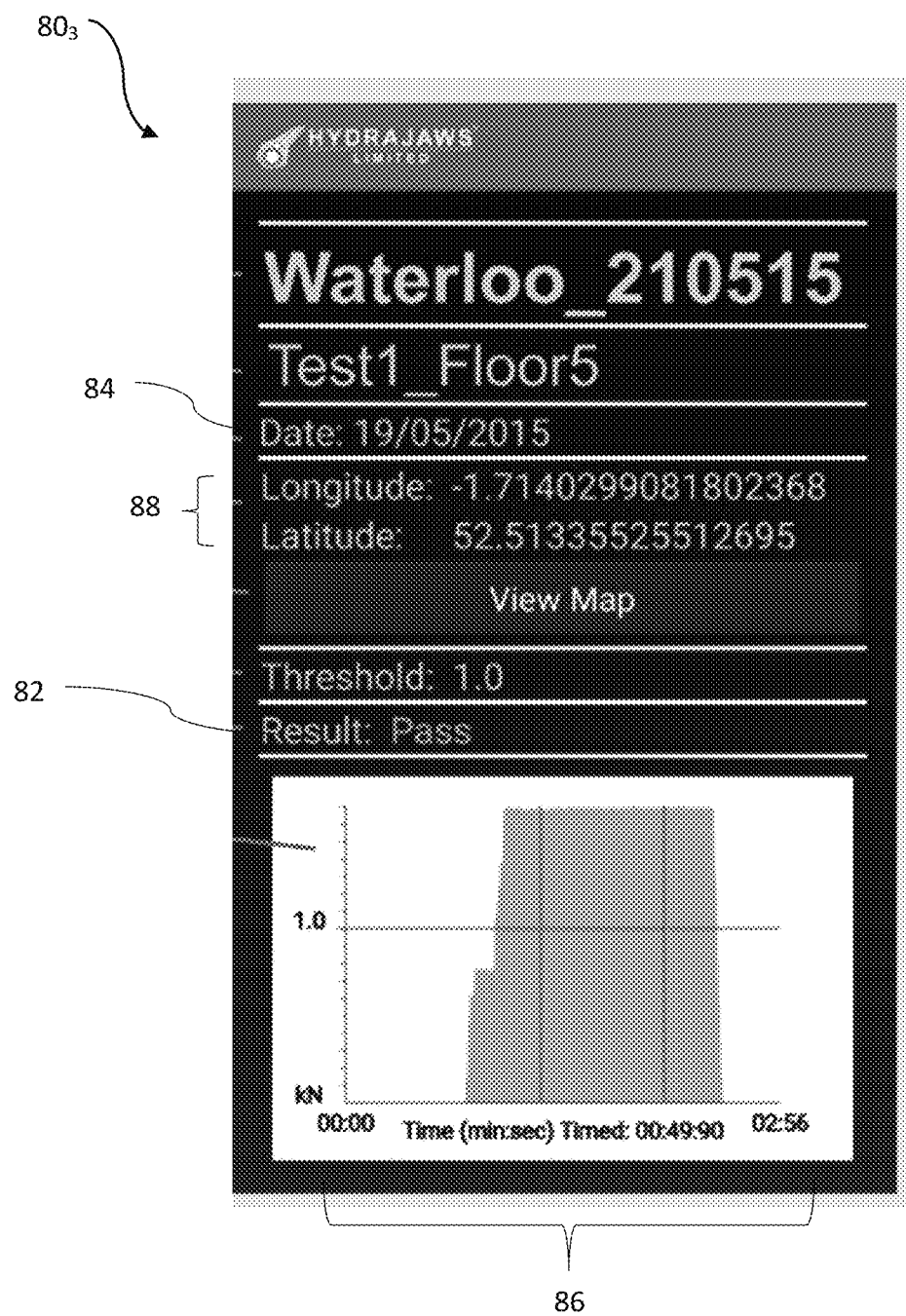

Embodiments of data system 48 may communicate with reporting system 50, which may include a display 60 configured to visually indicate the increasing force, F, on the digital load gauge 34, as well as a report-generation module 62. In this embodiment, report-generation module 62 may be configured to generate one or more testing reports $80_{1-n}$ based upon the force and/or displacement information measured by load cell 28 and displacement sensor 33, the date and time information tracked by timing device 58, and the geolocation information tracked by location module 54. Testing report $80_{1-n}$ may take any appropriate form and include and/or summarize any information relevant to the the testing. For example, a testing report $80_1$ may include a graphical representation of the force information (i.e., the increasing force, F, or a holding force, $F_{hold}$, applied to fastener 36) versus the time information (i.e., the incremental time frame of the testing), as shown in FIG. 5A. Embodiments of testing report $80_{1-n}$ may optionally incorporate displacement information, as shown in testing report $80_2$ of FIG. 5B. In one embodiment shown in FIG. 5C, testing report $80_3$ may include a pass-fail indication 82 associated with the testing based on predetermined testing criteria, and provide a confirmation of the date of the testing 84, a time frame of the testing 86, and a location 88 of test system 20 during the time frame 86 of the testing.

Returning to FIG. 4, embodiments of transmission system 52 may communicate with reporting system 50 and/or data system 48 and may be configured to communicate wirelessly with a number of client devices, located both at the testing site and located at sites remote to the testing site (e.g., a client's office, a testing technician's base office). In one embodiment, transmission system 52 may include a Bluetooth transceiver 64 configured to transmit to one or more local devices (e.g., located at the testing site) located within Bluetooth transmission range. In another embodiment, transmission system 52 may incorporate a mobile cellular network (e.g., a 3G or 4G network) transceiver 66 and/or a Wi-Fi transceiver 68, each configured to transmit to a remotely located client device via a distributed network. Client devices may include any appropriate and/or preferred computing devices such as, for example, a tablet computer 70, a smartphone 72, and/or a desktop/laptop computer 74. Transmission system 52 may also incorporate a USB port 76 to enable a wired transfer of data and/or a testing report directly between load gauge 34 and a client device 70, 72, 74.

Figure 6A:
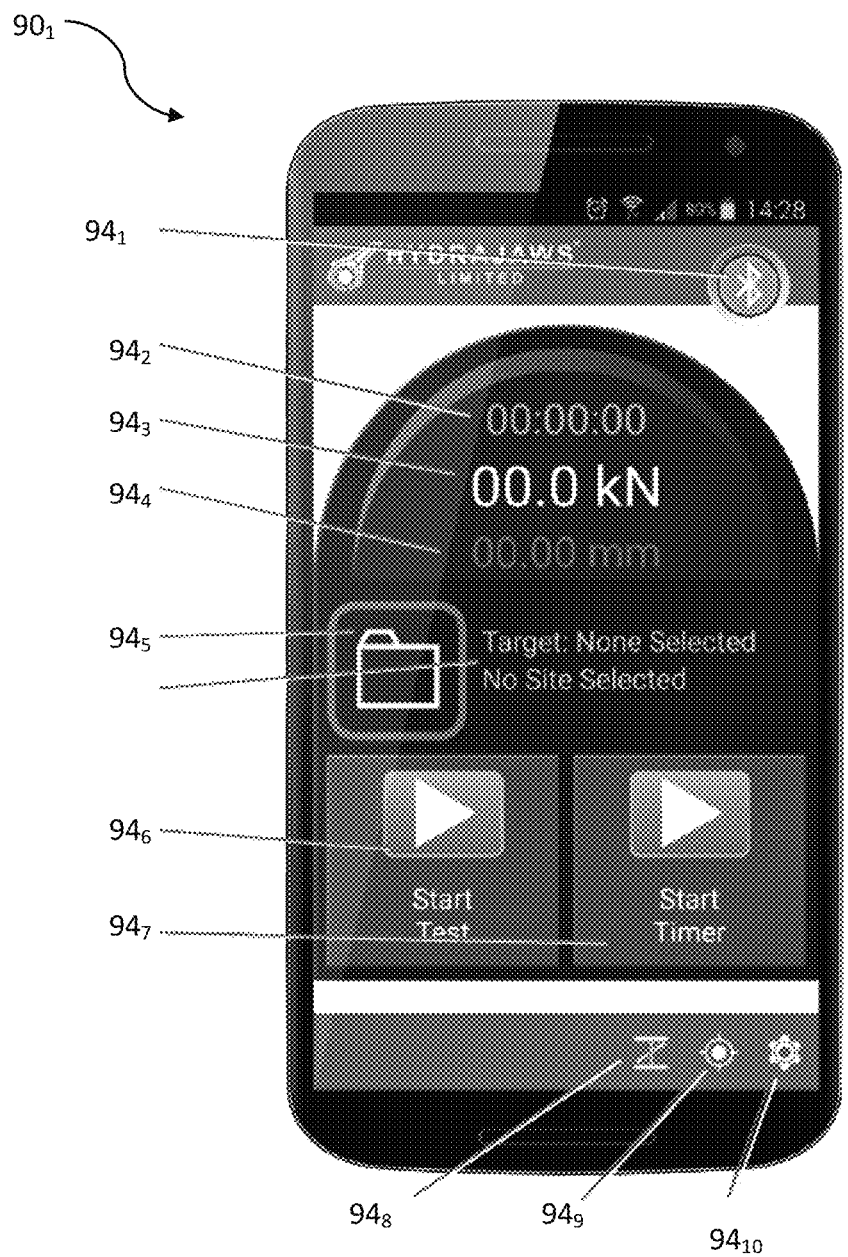
FIGS. 6A-6B provide screenshots showing exemplary graphical user interfaces associated with the digital testing and communication system of FIG. 4.
Figure 6B:
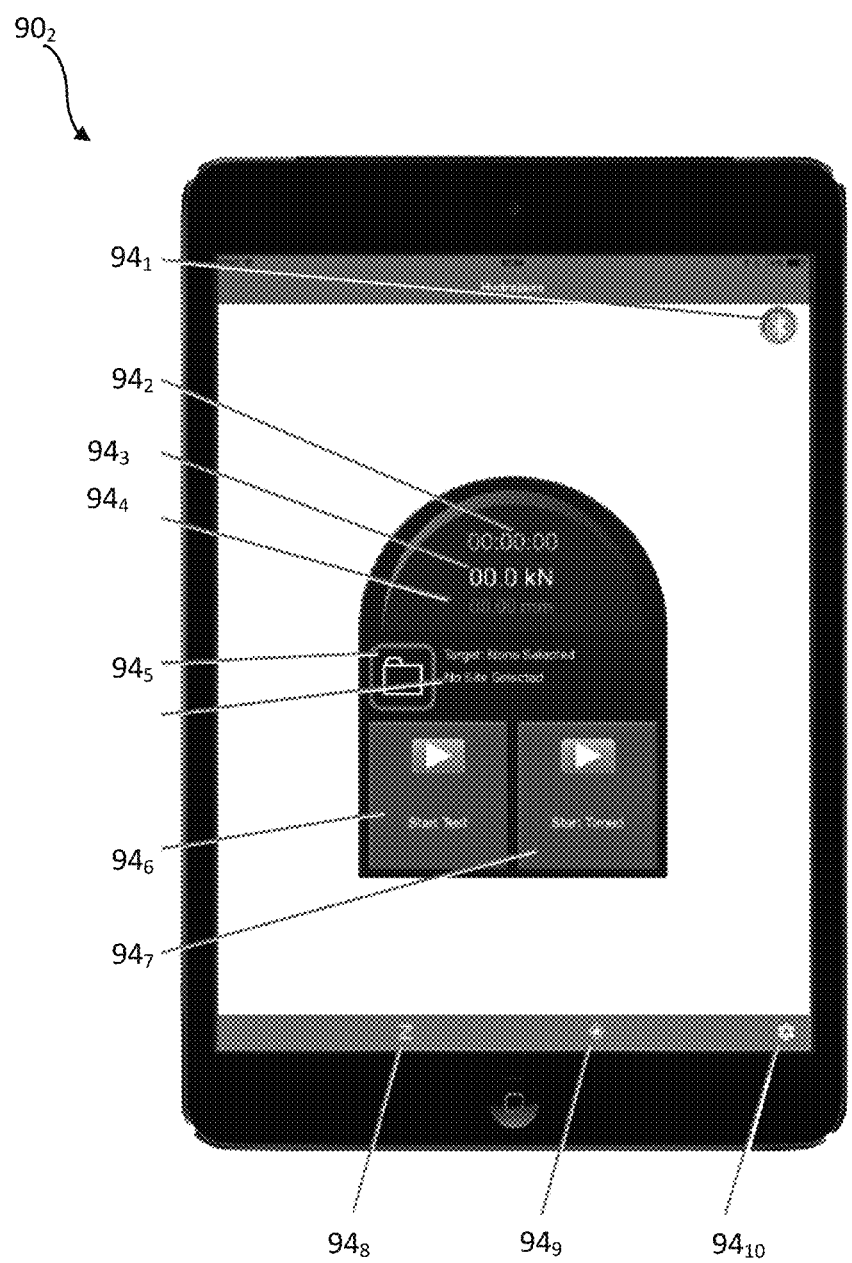

Testing software application 51 may be loaded or installed onto client device 70, 72, 74 in any appropriate manner. For example, application 51 may be directly transferred from a memory device such as a USB memory stick, or application 51 may be loaded from an email attachment, downloaded from an online application storefront such as, for example, the Apple App Store or Google Play, or downloaded from a proprietary website (e.g., www.hydrajaws.co.uk). Once downloaded and installed onto client device 70, 72, 74, a user may interact with testing and communication system 49 via a graphical user interface (GUI) 90 associated with testing software application 51. FIGS. 6A-6B illustrate a GUI $90_1$ and a GUI $90_2$ tailored for Android and Apple devices (e.g., smartphones), respectively. The appearance of GUI 90 may vary slightly from one type of device to another, but functionality may remain constant.

As shown in FIGS. 6A-6B, GUIs $90_{1-2}$ may include a number of functional buttons or indicators $94_{1-n}$, which enable a user to interact with system 49 to input test operating instructions and view customized reports $80_{1-n}$. In one embodiment, these buttons or indicators $94_{1-n}$ may include, for example, a Bluetooth connect button $94_1$, a timer $94_2$, a load applied indicator $94_3$, a displacement indicator, $94_4$, a test site folders button $94_5$ providing network access to testing reports for the current testing site, a test start button $94_6$, a timer button $94_7$, a zero-load and/or displacement indicator $94_8$, a GPS indicator $94_9$, and a displacement measurement toggle (on/off) $94_{10}$.

Using GUI 90, a user may pair a Bluetooth connection with digital load gauge 34 and/or communicate with gauge 34 via any other appropriate means. In one embodiment, the user may operate system 49 via GUI 90 to start tests, stop tests, track test progress, and generate and review test reports $80_{1-n}$. The ability to provide real-time reporting directly from the testing site provides engineers, clients, and other stakeholders with visual confirmation of the test and its date, location, and time frame. This summary information is helpful in confirming testing of the correct fastener and in justifying/verifying the time spent on site completing the test. Real-time, wireless reporting from a digital system that eschews manual logging of applied forces and time intervals also provides stakeholders with accurate and immediate graphical and summary information that may be viewed by testing professionals together with clients to examine why tests may not have met required standards. Once generated, testing reports may be linked to other reports generated at the same location or to a summary report comparing tests performed at the same location on different dates (e.g., year to year).

Figure 7:
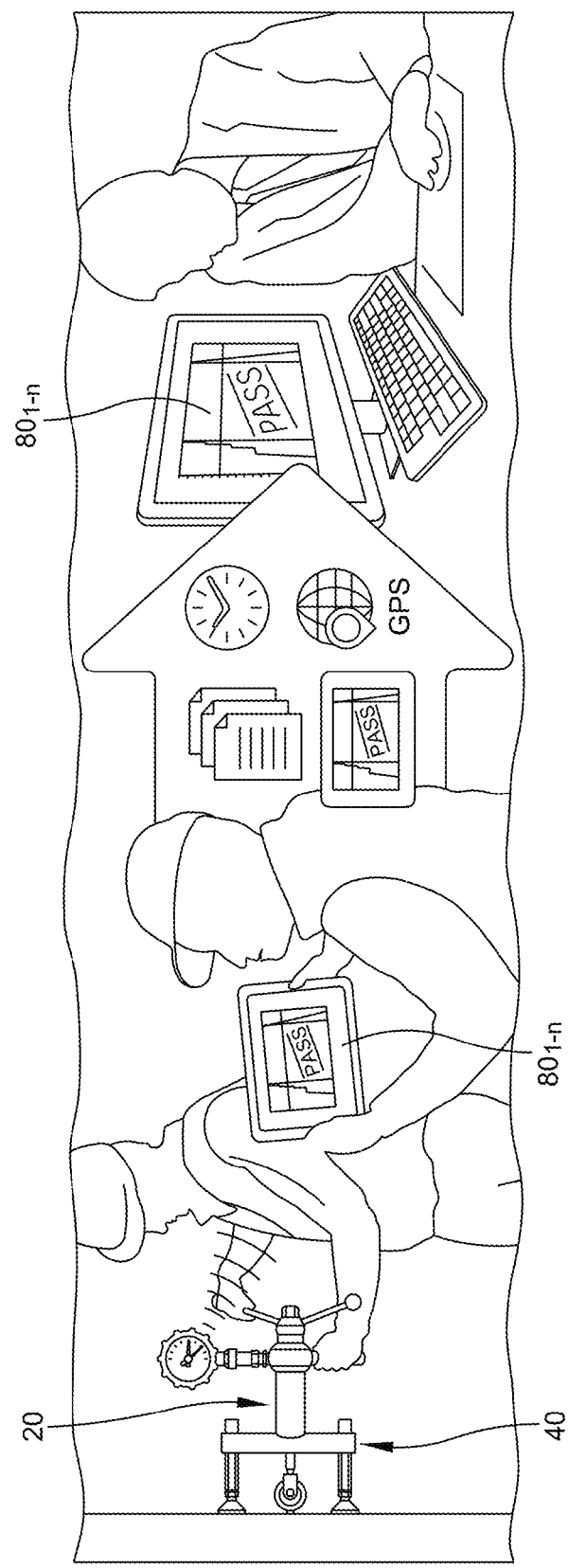
FIG. 7 illustrates a perspective view of two technicians performing a digital strength test featuring automated, wireless reporting via the digital testing and communication system of FIG. 4.

FIG. 7 illustrates a perspective view of a montage of two technicians performing a digital strength test having automated, wireless reporting. The figure summarizes a number of benefits provided by digital testing and communication system 49, discussed above, in that system 49 generates a testing report $80_{1-n}$, which is wirelessly provided in real-time to a stakeholder for further examination.

Initially, digital testing captures more efficient and accurate test results. Rather than a human operating a timer and manually recording force levels at timed intervals, digital force measurements are automatically and electronically recorded. This allows for increased measurement resolution and accuracy, and reduces the risks associated with human inattention and error, present both during the testing process and post-test when the results must be transcribed for presentation and storage. In addition, real-time reporting provides automatic accountability for time spent testing on-site in that it provides real-time proof of test data, job details, and job traceability. In addition, providing test results electronically from the testing site to clients and other stakeholders, whether located on-site or at a remote location, saves both time and unnecessary paperwork. Both clients and insurance companies can benefit from this type of transparency and traceability in meeting their compliance requirements.

Figure 8:
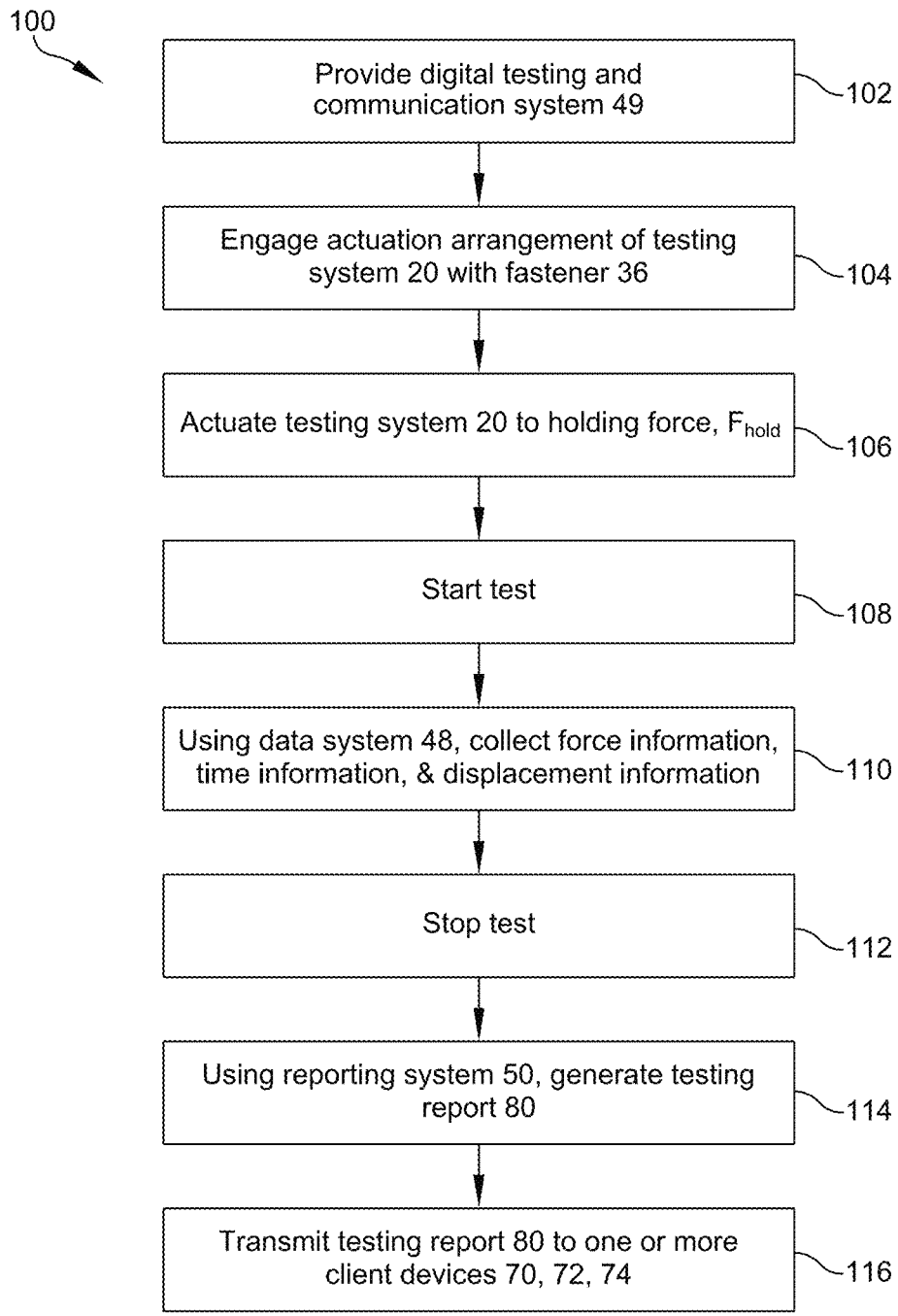
FIG. 8 provides a flow chart depicting an exemplary method for strength testing a fastener using embodiments of the digital testing and communication system of FIG. 4.

FIG. 8 provides a flow chart depicting an exemplary method 100 for strength testing fastener 36 using digital testing and communication system 49. In this embodiment, method 100 begins with providing digital testing and communication system 49 (102) and engaging the mechanical screw/actuation arrangement 26 of testing system 20 with the fastener to be tested (104). Once testing system 20 is engaged, a user may manually actuate system 20 (106) by rotating operating handle 24 to apply the increasing tensile force, F, to the fastener to reach desired holding force, $F_{hold}$ (106), before utilizing GUI 90 to start the test (108). Data system 48 may collect force information, time information, and/or displacement information (110), which may include a comparison to predetermined test criteria defining pass/fail limits, etc. When a desired holding time has elapsed, the user may employ GUI 90 to stop the test (112). The force, time, and displacement information and analysis may then be transferred to reporting system 50, such that report-generation module 62 may generate testing report 80 (114) including confirmation of the testing as well as a summary of the testing results. Transmission system 52 may then transmit testing report 80 to or between one or more client devices 70, 72, 74 (116), located either at the testing site or at a remote location.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A digital testing and communication system for testing a pull-out strength of a fastener member secured in a base material, comprising:
   a load cell;
   a mechanical actuation arrangement configured to engage with the fastener member and act through the load cell to apply a tensile force to the fastener member, the load cell configured to measure force information reflecting the tensile force applied to the fastener member;
   a digital load gauge communicatively coupled with the load cell;
   a displacement sensor communicatively coupled with the digital load gauge, the displacement sensor configured to measure displacement information reflecting a displacement of the fastener member;
   a data system, the data system including:
      a global positioning system (GPS) receiver configured to track geolocation information associated with the testing;
      a timing device configured to track date information and time information associated with the testing; and
      a load and displacement module configured to analyze the force information measured by the load cell throughout the testing;
   a transmission system, the transmission system configured to transmit the force information to a client device, wherein the load and displacement module is configured to analyze the displacement information, and wherein the transmission system is configured to transmit the displacement information to the client device; and
   a reporting system, the reporting system including a report-generation module configured to generate a testing report based on at least the force information.

2. The system of claim 1, wherein the transmission system includes a Bluetooth transceiver, and wherein the client device is located at a site of the testing.

3. The system of claim 1, wherein the transmission system includes at least one of a Wi-Fi transceiver and a mobile cellular transceiver, and wherein the client device is located remote to the site of the testing.

4. The system of claim 1, wherein the client device is selected from a group including a desktop computer, a laptop computer, a tablet computer, and a smartphone.

5. The system of claim 1, wherein the testing report comprises a graphical representation of the force information versus the time information.

6. The system of claim 5, wherein the testing report further comprises a graphical representation of the displacement information.

7. The system of claim 1, wherein the testing report comprises a pass-fail indication associated with the testing and an indication of a testing date, a testing time frame, and a geolocation of the apparatus during the testing date and the testing time frame.

* * * * *